(12) United States Patent
Mukkamala

(10) Patent No.: US 6,602,831 B2
(45) Date of Patent: Aug. 5, 2003

(54) OIL-SOLUBLE ADDITIVES FOR LUBRICATING OILS

(75) Inventor: Ravindranath Mukkamala, Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/054,058

(22) Filed: Jan. 22, 2002

(65) Prior Publication Data

US 2002/0142921 A1 Oct. 3, 2002

Related U.S. Application Data

(60) Provisional application No. 60/263,776, filed on Jan. 24, 2001.

(51) Int. Cl.⁷ .......................................... C10M 157/06
(52) U.S. Cl. ..................................................... 508/284
(58) Field of Search ........................ 508/284; 548/325.1

(56) References Cited

U.S. PATENT DOCUMENTS

| | | | | |
|---|---|---|---|---|
| 4,188,297 A | 2/1980 | Jayne et al. | ................ | 508/322 |
| 4,189,587 A | 2/1980 | Holt et al. | ................... | 548/312 |
| 4,589,991 A | 5/1986 | Ryer et al. | ................... | 508/276 |
| 4,661,273 A | 4/1987 | Frangatos et al. | .......... | 548/142 |
| 4,917,809 A | 4/1990 | Zinke et al. | ................. | 508/271 |
| 5,057,612 A | 10/1991 | Worley et al. | .............. | 548/301 |
| 5,318,712 A | 6/1994 | Lange et al. | ................. | 508/274 |
| 5,597,785 A | 1/1997 | Karol | .......................... | 508/274 |
| 6,187,722 B1 | 2/2001 | Rowland et al. | ............ | 508/284 |

FOREIGN PATENT DOCUMENTS

| | | |
|---|---|---|
| EP | 0380814 B1 | 8/1994 |
| EP | 0728747 A1 | 8/1996 |
| GB | 1053716 | 1/1967 |
| WO | WO 01/62739 A2 | 8/2001 |

OTHER PUBLICATIONS

D.F. Bushey et al.; Syntheses adn Stereochemistry of Ami-doximes, J. Org. Chem, 45 (21) pp. 4198–4206 (1980).
M.D. Nair et al.; Dispiroimidazolidinethiones, Indian J. Org. Chem, 5 pp. 290–293 (1967).
W. J. Middleton et al.; Fluorinated Aminoimidazolines. Synthesis and Determination of Tautomeric Structure, J. Org. Chem, 35 (5) pp.1480–1485 (1970).
F. Asinger et al.; Zum Substitutionsverhalten von Imidazolidin–4–thionen, Monatshefte fur chemie 107 pp. 35–41 (1976) (in German).
M. A. Voinov et al.; Reactions of Aldonitrones (3–Imidazolines–3–oxide Derivatives) with isothiocyanates 11, pp. 2642–2647 (1992) (in Russian).
John D. Christian; Imidazolidinethiones; J. Org. Chem. vol. 22; pp. 396–399 (1957).
Martino Paventi et al.; Canadian Journal of Chemistry; vol. 65; pp. 282–289 (1987).
Te–Chen Tsao et al.; Novel N–Halamine Disinfectant Compounds; Biotechnol. Prog., vol. 7,; pp. 60–66 (1991).
A E. Oberster, et al.; New Nondiscoloring Stabilizer System For SBR and Stereospecific Diene Polymers; Rubber Chemistry and Technology; pp. 255–270; (1968).

*Primary Examiner*—Ellen M. McAvoy
(74) *Attorney, Agent, or Firm*—Kenneth Crimaldi

(57) ABSTRACT

A compound of formula I:

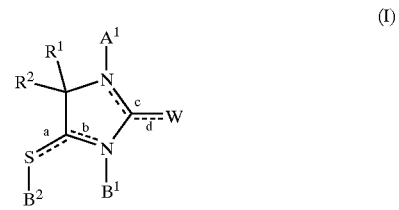

wherein W represents O, S—$A^2$, or two groups, $R^3$ and $R^4$; bonds a and b are single or double bonds, provided that one of a and b is a single bond and the other is a double bond; c is a single or double bond, and d is a single bond, double bond, or two single bonds, provided that d is a single bond when c is a double bond, d is not a single bond when c is a single bond, and W is $R^3$ and $R^4$ when d is two single bonds;

$A^1, A^2$, B and $B^2$ are independently hydrogen, alkyl, alkenyl, aralkyl or one of the groups depicted in Scheme 1:

Scheme 1

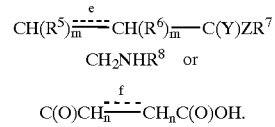

13 Claims, No Drawings

OIL-SOLUBLE ADDITIVES FOR LUBRICATING OILS

CROSS REFERENCE TO RELATED PATENT APPLICATIONS

This is a non-provisional application of prior U.S. provisional application Ser. No. 60/263,776 filed Jan. 24, 2001.

BACKGROUND

This invention relates generally to heterocyclic compounds useful as ashless oil-soluble additives for lubricating oils.

Zinc dialkyldithiophosphates (ZDDP) are widely used as lubricant additives. The principal disadvantages of these compounds are that an ash residue is produced by the zinc as the additive is consumed, and that phosphorus is known to affect the efficiency of catalytic converters in motor vehicles, thereby causing emissions problems. An ashless, non-phosphorus alternative to ZDDP would be extremely useful.

Dithiohydantoin compounds are disclosed in European Patent Application No. EP 0 728 747 A1. However, the compounds are not within the scope of the present invention, and moreover, are disclosed only for pharmaceutical applications.

The problem addressed by this invention is to find improved phosphorus-free ashless oil-soluble additives for lubricating oils.

Statement of Invention

The present invention is directed to a compound of formula I:

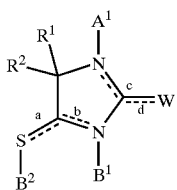

(I)

wherein W represents O, S—$A^2$, or two groups, $R^3$ and $R^4$; bonds a and b are single or double bonds, provided that one of a and b is a single bond and the other is a double bond; c is a single or double bond, and d is a single bond, double bond, or two single bonds, provided that d is a single bond when c is a double bond, d is not a single bond when c is a single bond, and W is $R^3$ and $R^4$ when d is two single bonds; $A^1$, $A^2$, $B^1$ and $B^2$ are independently hydrogen, alkyl, alkenyl, aralkyl or one of the groups depicted in Scheme 1:

Scheme 1

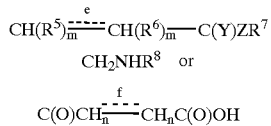

provided that $B^1$ is absent when b is a double bond, $B^2$ is absent when a is a double bond, $A^1$ is absent when c is a double bond and $A^2$ is absent when d is a double bond; and provided that $A^2$ or $B^2$ is not aralkyl when W is O or S—$A^2$; $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; Y is O or S; Z is O, S or $NR^9$; m is 0 when bond e is a double bond and 1 when e is a single bond; n is 1 when bond f is a double bond and 2 when f is a single bond; $R^5$ is $C(Y)ZR^7$, hydrogen or $C_1$–$C_4$ alkyl; $R^6$ is hydrogen or $C_1$–$C_4$ alkyl; $R^7$, $R^8$ and $R^9$ are independently hydrogen, alkyl, alkenyl, aryl or aralkyl;

provided that at least one of $A^1$, $A^2$, $B^1$ and $B^2$ is present and is not hydrogen.

The present invention is further directed to a composition comprising a lubricating oil and from 0.1 to 20% of a compound of formula I; and to a method for improving the anti-wear and anti-corrosion characteristics of a lubricating oil by adding from 0.1 to 20% of a compound of formula I.

DETAILED DESCRIPTION

An "alkyl" group is a hydrocarbyl group having from one to twenty carbon atoms in a linear, branched or cyclic arrangement, and having from 0 to 2 oxygen, nitrogen or sulfur atoms. Substitution on alkyl groups of one or more halo, hydroxy, alkoxy, alkanoyl or amido groups is permitted; alkoxy, alkanoyl and amido groups may in turn be substituted by one or more halo substituents. Preferably, alkyl groups contain from one to twelve carbon atoms and from 0 to 1 oxygen, nitrogen or sulfur atoms. An "alkenyl" group is an "alkyl" group in which at least one single bond has been replaced with a double bond. An "aryl" group is a substituent derived from an aromatic compound, including heterocyclic aromatic compounds having heteroatoms chosen from among nitrogen, oxygen and sulfur. An aryl group has a total of from five to twenty ring atoms, and has one or more rings which are separate or fused. Substitution on aryl groups of one or more halo, alkyl, alkenyl, hydroxy, alkoxy, alkanoyl or amido groups is permitted, with substitution by one or more halo groups being possible on alkyl, alkenyl, alkoxy, alkanoyl or amido groups. An "aralkyl" group is an "alkyl" group substituted by an "aryl" group.

In formula I and Scheme 1, the letter a, b, c, d, e or f represents the total bonding between the atoms adjacent to each letter, e.g., when "a" represents a single bond, the sulfur atom and ring carbon to which it is attached are connected by a single bond. These letters are used in formula I to indicate that the compound may exist in different tautomeric forms, e.g., when the sulfur shown in formula I is substituted, i.e., $B^2$ is present, a is a single bond, b is a double bond and $B^1$ is absent, as will be understood by one skilled in the art. In the substituent groups of Scheme 1, e and f indicate whether the bond between the adjacent carbons is a single or double bond, which is determined by the alkylating agent used to introduce the substituent, as described hereinbelow.

It is preferred that at least one of $A^1$, $A^2$, $B^1$ and $B^2$ is present and is not hydrogen or methyl. It is also preferred that $A^1$, $A^2$, $B^1$ and $B^2$ are independently hydrogen or one of the three groups depicted in Scheme 1. It is also preferred that W is $R^3$ and $R^4$, and c is a single bond. It is also preferred that W is $R^3$ and $R^4$, c is a single bond, $A^1$ is hydrogen, and $B^1$ or $B^2$ is one of the groups depicted in Scheme 1.

In one aspect of the invention, a tetraalkylimidazolidinethione (TAIT), or an imidazolidinethione having from one to three alkyl groups, is alkylated with an acrylate ester to produce a compound having a $CHR^5CHR^6C(O)OR^7$ group, as shown below for $R^5=R^6=H$ and $R^7=$alkyl. If $R^1$, $R^2$, $R^3$ and $R^4$ are all methyl, the TAIT is known as TMIT.

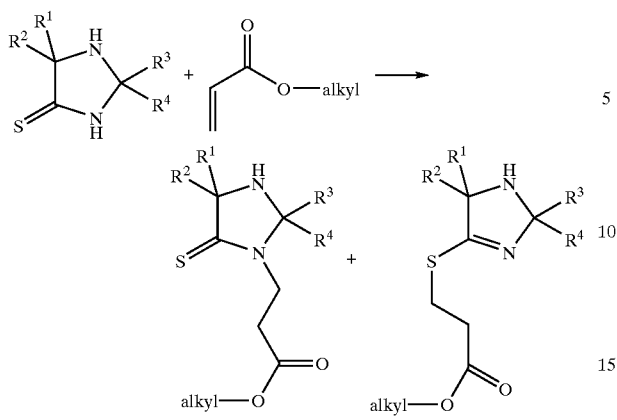

The extent of N-alkylation versus S-alkylation varies with the identity of the R groups on the imidazolidenethione ring and with the alkylating agent, as shown below in the Examples.

In another aspect of this invention, a TAIT or an imidazolidinethione having from one to three alkyl groups is alkylated with an alkyl propiolate to produce a compound in which the ester side chain has a carbon-carbon double bond. In another aspect of this invention, a TAIT or unsubstituted imidazolidinethione is alkylated with an imine, $CH_2=NR^8$. In another aspect of this invention, a TAIT or an imidazolidinethione having from one to three alkyl groups is alkylated with maleic or succinic anhydride to produce a compound having a $C(O)CH=CHC(O)OH$ or $C(O)CH_2CH_2C(O)H$ side chain, respectively, with alkylation occurring mainly on the sulfur.

In one embodiment of the invention, the group $ZR^7$ in a $CHR^5CHR^6C(Y)ZR^7$ side chain or a $CH=CHC(Y)ZR^7$ side chain contains a thioethyl group, i.e., a group having the structure —$CH_2CH_2S$—, where one of the $CH_2$ and the sulfur is attached to the C(Y) functionality and the other is attached to an alkyl, alkenyl or aralkyl group. For example, $ZR^7$ can be $OCH_2CH_2S$—R, where R is alkyl, alkenyl or aralkyl; when Y is O, and $R^5$ and $R^6$ are H, the side chain is $CH_2CH_2C(O)OCH_2CH_2S$—R.

In a preferred embodiment of the invention, from 0.1 to 10% of a compound of formula I is added to a lubricating oil. More preferably, from 0.5 to 10% of a compound of formula I is added to a lubricating oil, and most preferably, from 0.5 to 3%. A lubricating oil is a natural or synthetic oil, having suitable viscosity for use as a lubricant, or a mixture thereof.

EXAMPLES

Example 1

Alkylation of Tetraalkylimidazolidinethiones with Alkyl Acrylates

TMIT was prepared according to the procedure given in U.S. Pat. No. 5,057,612, as follows.

To a mechanically-stirred mixture of ammonium sulfide (0.4 moles, 136 mL, 20 wt % aqueous solution), sodium cyanide (14.7 g, 0.3 moles), ammonium chloride (16.1 g, 0.3 moles) and water (80 mL), acetone (44 mL, 0.6 moles) was added drop-wise over a period of 30 min.; during the addition of acetone, the reaction temperature rose to about 36° C. The reaction mixture was then externally heated to 65° C. for a period of 6–7 hours. The reaction mixture was cooled to 0–5° C. using an ice bath, and the white solid was filtered, washed with cold water and suction-dried. The yield of TMIT was 44.6 grams (94 %); melting point: 155° C. IR: 3521, 2976, 1657, 1524, 1462 cm$^{-1}$; $^1$H NMR (CDCl$_3$, 500 MHz): δ1.46 (s, 6 H), 1.44 (s, 6 H) ppm; $^{13}$C NMR (CDCl$_3$, 125 MHz): δ207.7, 78.4, 70.9, 29.9, 29.9 ppm.

7,14-diazadispiro [5.1.5.2]pentadecane-15-thione (DDPT),

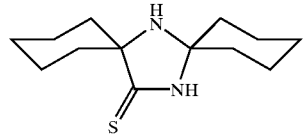

was prepared according to the procedure described for TMIT from ammonium sulfide (0.4 moles, 136 mL, 20 wt % aqueous solution), sodium cyanide (14.7 g, 0.3 moles), ammonium chloride (16.1 g, 0.3 moles) and water (80 mL); with addition of cyclohexanone (58.8 g, 0.6 moles). The product was obtained as a white solid (69.8 grams, 98%), and melted at 229° C. IR: 3127, 2925, 2855, 1516, 1454 cm-1; $^1$H NMR (CDCl$_3$, 500 MHz): δ9.8 (bs, 1H), 1.9(dt, 2H), 1.8–1.2 (m, 18H) ppm; $^{13}$C NMR (CDCl$_3$, 125 MHz): δ207.8, 81.0, 72.9, 39.6, 37.8, 24.9, 24.6, 23.0, 21.9 ppm.

Unless otherwise specified, tetraalkylimidazolidinethiones were allowed to react with alkyl acrylates in acetonitrile in the presence of 50 mole % of Cs$_2$CO$_3$ at room temperature for 10–15 hours (TMIT) or for 5 hours (DDPT) to produce compounds having the following structure:

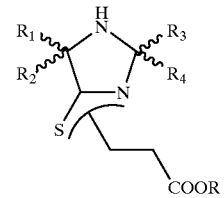

Detailed procedures and product analyses for several products are presented in Examples 2–8. The acrylates are abbreviated as follows: MA=methyl acrylate; 2-EHA=2-ethylhexyl acrylate; LA=lauryl acrylate; BA=butyl acrylate; and TUA=3-thiaundecyl acrylate. Yield is given in %, the ratio of N-alkylated adduct to S-alkylated adduct (N/S) as a ratio of percentages or as "nd" (not determined), the physical state (state) as "L" (liquid), "SS" (soft solid) or "SG" (sticky gum), and the oil solubility (oil sol) as a weight percent. Oil solubility was measured at room temperature in EXCEL HC 100 lubricating base oil (available from Pennzoil Corp.). The adduct ratio, N/S, was determined from integration of proton NMR signals. The results for all acrylate adducts are presented below in Table 1.

Example 2

Adduct of TMIT and 2-EHA

A mixture of TMIT (1.0 g, 6.33 mmol), 2-ethylhexyl acrylate (1.16 g, 6.33 mmol) and cesium carbonate (1.0 g, 3.3 mmol) in acetonitrile (15 mL) was stirred at room temperature for 24 h. The reaction mixture was filtered to separate solid cesium carbonate and solvent was evaporated from the filtrate to obtain the product as a colorless oil (1.9 g, 88 %). IR: 3325, 2961, 1732, 1595, 1480 cm$^{31}$ $^1$; $^1$H NMR (CDCl$_3$, 500 MHz): δ3.96 (overlapping d, 2 H), 3.83 (t, 1.72 H), 3.22 (t, 0.28 H), 2.82 (t, 1.72 H), 2.71 (t, 0.28 H), 1.91

(bs, 1H), 1.42 (s, 6 H), 1.40 (s, 6H), 1.35–1.20 (m, 8 H), 0.85 (overlapping t, 6 H) ppm; $^{13}$C NMR (CDCl$_3$, 125 MHz): δ205.8, 173.6, 171.9, 171.3, 130.2, 128.5, 88.7, 82.9, 70.35, 69.6, 67.2, 66.9, 66.8, 40.6, 38.6, 33.9, 31.4, 30.26, 30.21, 28.79, 28.71, 28.23, 25.8, 23.64, 22.83, 13.9, 10.9 ppm.

Example 3

Adduct of TMIT and LA

A procedure similar to that of Example 2 was used. Starting from TMIT (1.0 g, 6.33 mmol), lauryl acrylate (1.5 g, 6.33 mmol) and cesium carbonate (1.0 g, 3.3 mmol) in acetonitrile (15 mL), the product was isolated as a colorless oil (1.7 g, 68 %). IR: 3326, 2925, 1732 1596, 1480 cm$^{-1}$; $^1$H NMR (CDCl$_3$, 500 MHz): δ4.18 (overlapping d, 2H), 3.86 (t, 1.78 H), 3.36 (t, 0.22 H), 2.85 (t, 1.78 H), 2.75 (t, 0.22 H), 1.90 (bs, 1H), 1.62 (m, 2H), 1.48 (s, 6H), 1.44 (s, 6H), 1.4–1.2 (m, 18 H), 0.88 (t, 3H) ppm.

Example 4

Adduct of TMIT and BA

A procedure similar to that of Example 2 was used. Starting from TMIT (1.0 g, 6.33 mmol), n-butyl acrylate (0.81 g, 6.33 mmol) and cesium carbonate (1.0 g, 3.3 mmol) in acetonitrile (15 mL), the product was isolated as a colorless oil (1.3 g, 72 %). IR: 3323, 2961, 1732, 1582, 1483 cm$^{-1}$; $^1$H NMR (CDCl$_3$, 500 MHz): δ4.08 (t, 2H), 3.85 (t, 2H), 2.84 (t, 2H), 1.95 (bs, 1 H), 1.60 (m, 2H), 1.46 (s, 6H), 1.42 (s, 6H), 1.36 (m, 2H), 0.91 (t, 3H) ppm.

Example 5

Adduct of DDPT and LA

A procedure similar to that of Example 2 was used. Starting from DDPT (1.0 g, 4.2 mmol), lauryl acrylate (1.0 g, 4.2 mmol) and cesium carbonate (0.68 g, 2.1 mmol) in acetonitrile (25 mL), the product was isolated as a light-yellow, low-melting solid (1.9 g, 95 %). IR: 2927, 2845, 1733, 1474 cm$^{-1}$; $^1$H NMR (CDCl$_3$, 500 MHz): δ4.15 (t, 2H), 3.85 (t, 2H), 2.85 (t, 2H), 2.03 (dt, 2H), 1.8–1.2 (m, 38 H), 0.88 (t, 3H) ppm.

Example 6

Adduct of TAIT Mixture Prepared from Acetone/Methyl Isobutyl Ketone/Methyl Ethyl Ketone/Cyclohexanone and EHA A TAIT mixture was prepared from an equimolar mixture of the four title ketones according to the procedure used for preparation of TMIT, using ammonium sulfide (136 mL, 0.4 moles, 20 wt % aqueous solution), sodium cyanide (14.7 g, 0.3 moles), ammonium chloride (16.1 g, 0.3 moles), water (80 mL), cyclohexanone (14.7 g, 0.15 moles), acetone (8.7 g, 0.15 moles) ethyl methyl ketone (10.8 g, 0.15 moles), and methyl isobutyl ketone (15.0 g, 0.15 moles) to obtain an oily layer at the end of the heating period. The oil layer was extracted into chloroform (350 mL), washed with water and dried with anhydrous potassium carbonate. Solvent evaporation yielded the product as a thick oil that slowly turned into a sticky gray solid (36 grams, yield: 55 % for an average molecular weight of 220). IR: 3361, 2962, 2874, 1605, 1520, 1459 cm$^{-1}$; $^1$H NMR (CDCl$_3$, 500 MHz): δ2.24 (d), 2.06 (s), 1.85–1.91 (m), 1.86–1.56 (m), 1.50–1.46 (m), 1.45–1.34 (m), 1.26–1.11 (bm), 1.39 (t), 0.99 (dd), 0.95–0.84 (m) ppm; $^{13}$C NMR (CDCl$_3$, 125 MHz): δ207.8, 207.62, 207.60, 207.43, 207.40, 207.01, 206.89, 206.68, 206.66, 81.6, 81.18, 81.14, 80.70, 80.65, 78.38, 78.31, 73.95, 73.30, 72.82, 70.79, 70.46, 70.18 and several peaks between 40–10 ppm.

A procedure similar to that of Example 2 was used for the reaction with 2-EHA. Starting from the TAIT product described in the preceding paragraph (1.0 g, ca. 4.5 mmol), 2-ethylhexyl acrylate (0.82 g, 4.5 mmol) and cesium carbonate (0.75 g, 2.25 mmol) in acetonitrile (20 mL), the product was isolated as a yellow oil and solid mixture (1.8 g, 99 %). IR: 3325, 2933, 2860, 1732, 1480 cm$^{-1}$.

Example 7

Adduct of TAIT Mixture Prepared from Methyl Ethyl Ketone and BA

A cis-trans TAIT mixture was obtained by applying the procedure used for preparation of TMIT to ammonium sulfide (136 mL, 0.4 moles, 20 wt % aqueous solution), sodium cyanide (14.7 g, 0.3 moles), ammonium chloride (16.1 g, 0.3 moles), water (80 mL), and ethyl methyl ketone (54.1 g, 0.75 moles) to obtain an oily layer at the end of the heating period. The oil layer was extracted into chloroform (350 mL), washed with water and dried with anhydrous potassium carbonate. Solvent evaporation yielded the product as a thick oil that turned into a sticky dirty-white solid. This solid was washed quickly with cold water and suction dried to give a white powder (23 g, yield: 41%) that melted at 72° C. IR: 3320, 3128, 2966, 1533, 1457, 1371 cm$^{-1}$; $^1$H NMR (CDCl$_3$, 500 MHz): δ1.85–1.65 (m, 4H), 1.44–1.36 (4s, 6H), 0.99–0.91 (m, 6H) ppm; $^{13}$C NMR (CDCl$_3$, 125 MHz): δ207.15, 207.07, 81.24, 81.17, 73.69, 73.51, 35.49, 34.99, 33.85, 33.56, 28,56, 28.29, 27.82, 27.24, 8.55, 8.46, 8.25 ppm.

A procedure similar to that of Example 2 was used for the reaction with BA. Starting from the TAIT product described in the preceding paragraph (4.0 g, 21.5 mmol), n-butyl acrylate (2.8 g, 21.5 mmol) and cesium carbonate (3.5 g, 10.8 mmol) in acetonitrile (50 mL), the product was isolated as a yellow oil (6.1 g, 90%). IR: 3351, 2965, 2875, 1732, 1482 cm$^{-1}$; $^1$H NMR (CDCl$_3$, 500 MHz): δ4.05 (t, 2H), 3.95 (m), 3.80 (m), 3.63 (m), 2.95 (m), 2.82 (m), 2.67 (m), 1.80–1.51 (m, 6 H), 1.35 (m, 8H), 0.88 (m, 9H) ppm; $^{133}$C NMR (CDCl$_3$, 125 MHz): δ205.31, 205.05, 171.2, 85.77, 85.67, 72.44, 72.21, 64.48, 40.28, 34.55, 33.93, 32.65, 33.63, 31.06, 31.03, 30.38, 28.61, 28.21, 26.46, 26.33, 18.91, 13.49 ppm.

Example 8

Adduct of TMIT and 3-Thiaundecyl Acrylate

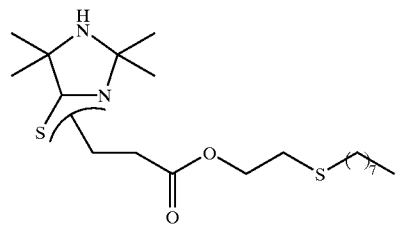

A procedure similar to that of Example 2 was used. Starting from TMIT (1.0 g, 6.33 mmol), 3-thiaundecyl acrylate (1.4 g, 6.33 mmol) and cesium carbonate (1.0 g, 3.3 mmol) in acetonitrile (20 mL), the product was isolated as a light yellow oil (2.0 g, 83 %). IR: 2961, 1734,1481 cm$^{-1}$;

$^1$H NMR (CDCl$_3$, 500 MHz): δ4.22 (t, 2H), 3.84 (t, 2H), 2.84 (t, 2H), 2.71 (t, 2H), 2.52 (t, 2H), 1.55 (m, 2H), 1.46 (s, 6H), 1.42 (s, 6H), 1.4–1.2 (m, 10H), 0.85 (t, 3H) ppm; $^{13}$C NMR (CDCl$_3$, 125 MHz): δ205.9, 170.9, 82.9, 69.5, 63.7, 40.4, 32.2, 31.6, 31.3, 30.2, 30.1, 29.5, 29.0, 28.6, 28.2, 22.4, 13.9 ppm.

TABLE 1

TAIT-Acrylate Ester Addition Products and Oil Solubilities

| Ex. No. | TAIT | acrylate | yield | N/S | state | oil sol |
|---|---|---|---|---|---|---|
|  | TMIT | MA | 85 | 83/17 | L | <2 |
| 2 | TMIT | 2-EHA | 88 | 86/14 | L | >20$^a$ |
| 3 | TMIT | LA | 68 | 89/11 | L | >20$^a$ |
| 4 | TMIT | BA | 72 | >97/<3 | L | <5 |
|  | DDPT | MA | 20 | >99/<1 | SS | <5 |
|  | DDPT | BA | 96 | >99/<1 | SS | <5 |
|  | DDPT | 2-EHA | 95 | >99/<1 | SG | ca. 5$^b$ |
| 5 | DDPT | LA | 95 | ca. 95/5 | SG | ca. 10$^b$ |
|  | mixture$^c$ | 2-EHA | 89 | nd | L | ca. 10 |
| 6 | mixture$^d$ | 2-EHA | 99 | nd | L | ca. 10 |
|  | mixture$^d$ | LA | 99 | nd | L/S | ca. 10 |
| 7 | mixture$^e$ | BA | 90 | nd | L | >10 |
| 8 | TMIT | TUA | 83 | >95/<5 | L | ca. 5 |

$^a$Miscible at room temperature to give a single clear phase.
$^b$The mixture with oil was an unclear dispersion, with the product from lauryl acrylate being more clear than that from 2-ethylhexyl acrylate.
$^c$TAIT produced from equimolar mixture of acetone/methyl isobutyl ketone/cyclohexanone.
$^d$TAIT produced from equimolar mixture of acetone/methyl isobutyl ketone/methyl ethyl ketone/cyclohexanone.
$^e$TAIT cis/trans mixture produced from methyl ethyl ketone.

Example 9

Efficacy Testing and Performance

Efficacy of four oil formulations was tested, including a base oil and one containing a commercial anti-wear ZDDP-based additive, ELCO-103. The samples tested were as follows: (1) EXCEL HC 100 base oil; (2) EXCEL HC 100 with 1% ELCO 103; (3) EXCEL HC 100 with 1% of the adduct of 2-EHA and TMIT (see Example 2); and (4) EXCEL HC 100 with 1% of an imine adduct of TMIT (see Example 15). Details of the tests are as follows:

4-Ball anti-wear test (ASTM D-4172). Load: 40 Kg; Temp: 75° C.; Rotation rate:1200 rpm; Time: 1 hour; Measured parameter: wear scar diameter in mm on the steel balls. The smaller the scar diameter, the more effective a given anti-wear additive.

Load carrying capacity (EP test, ASTM D-2783). Similar to the anti-wear test above, but starts at room temperature and the load on four rotating balls is constantly increased until the balls weld to each other. The quantities measured to assess performance are weld point load (kgf), scar diameter (mm at 100 kgf or 126 kgf) just before weld point, and load wear index (LWI) (average of sum of the corrected loads determined for 10 applied loads preceding the weld point, kgf). A higher LWI is an indication of better anti-wear properties.

Copper corrosion test (ASTM D-130). Copper metal specimens are immersed in the oil sample at 212° F. (100° C.) for three hours, and the appearance is then rated based on the tarnish acquired. Here, a lower rating reflects lesser corrosivity. For example, a rating of "1" indicates only a slight tarnish, with "1A" being a light orange and "1B" a dark orange; "2" would indicate moderate tarnish, with ratings of "A" through "E" indicating progressively darker colors.

Results of the tests are presented below in Table 2.

TABLE 2

Test Results for Lubricating Oils

| sample | ASTM D-4172 scar diameter | ASTM D-130 corrosion | EP Test scar diameter$^b$ | LWI |
|---|---|---|---|---|
| 1 | 0.84 | 1B$^a$ | 2.99 @ 100 | 10.8 |
| 2 | 0.64 | 1A$^a$ | 2.1 @ 100 | 21.5 |
| 3 | 0.63 | 1A$^a$ | 2.45 @ 100 | 14.5 |
| 4 | 0.65 | 1A$^a$ | 2.47 @ 126 | 18.8 |

$^a$Each sample has a slight tarnish.
$^b$The actual weld point of samples 1–3 was 126 kgf, and that of sample 4 was 160 kgf.

Example 10

Adduct of TMIT and Methyl Iodide

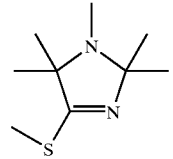

A mixture of TMIT (2.0 g, 12.6 mmol), methyl iodide (5.6 g, 40 mmol), and anhydrous potassium carbonate (8.3 g, 138. 2 mmol) in chloroform (45 mL) were stirred at room temperature for 2 days. The mixture was filtered, and solvent was evaporated to obtain the product depicted above as a liquid (1.9 g, 83%). $^1$H NMR (CDCl$_3$3, 500 MHz): δ2.38 (s, 3H), 2.26 (s, 3H), 1.25 (s, 6H), 1.16 (s, 6H) ppm; $^{13}$C NMR (CDCl$_3$, 125 MHz): δ175.1, 88.9, 70.3, 27.5, 26.4, 24.6, 12.6 ppm. The product was soluble in EXCEL HC 100 lubricating base oil only in an amount below 1% by weight.

Example 11

Adduct of DDPT and Methyl Iodide

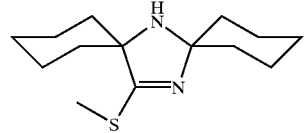

A mixture of DDPT (3.0 g, 12.6 mmol), methyl iodide (5.6 g, 40 mmol), and anhydrous potassium carbonate (8.3 g, 138. 2 mmol) in chloroform (30 mL) was stirred at room temperature for 2 days. The mixture was filtered, and solvent was evaporated to obtain the product as a thick liquid (2.45 g, 77%) that slowly turned into a soft solid. $^1$H NMR (CDCl$_3$, 500 MHz): δ2.41 (s, 3H), 1.75–1.1 (m, 20 H) ppm; $^{13}$C NMR (CDCl$_3$, 125 MHz): δ174.9, 90.5, 72.6, 40.3, 37.5, 25.4, 25.2, 23.4, 22.4, 13.5 ppm. The product was soluble in EXCEL HC 100 at 5 weight % at room temperature, and remained clear at room temperature after 1 week.

Example 12

Adduct of TMIT and Methyl Propiolate

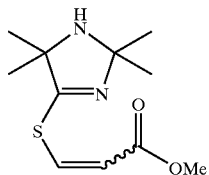

A mixture of TMIT (1.0 g, 6.33 mmol) and methyl propiolate (0.53 g, 6.33 mmol) in chloroform (15 mL) was stirred at room temperature for 24 h, followed by heating at 45° C. for another 24 h. Solvent evaporation yielded the product depicted above as a light-yellow, crystalline solid (1.4 g, 92%). IR: 3329, 2974, 1706, 1606, 1436 cm$^{-1}$; $^1$H NMR (CDCl$_3$, 500 MHz): δ8.29 (d, J=16.0 Hz, 0.12 H), 8.15 (d, J=10 Hz, 0.88 H), 6.16 (d, J=16 Hz, 0.12 H), 6.19 (d, J=10 Hz, 0.88 H), 3.7 (s, 3H), 1.47 (s, 0.72 H), 1.45 (s, 0.72 H), 1.42 (s, 5.3 H), 1.36 (s, 5.3 H) ppm; $^{13}$C NMR (CDCl$_3$, 125 MHz): δ171.4, 169. 6, 166.9, 141.3, 140.6, 118.9, 115.5, 114.1, 51.6, 30.5, 30.07, 30.06, 28.3 ppm. The product is an 85/15 mixture of cis/trans isomers. The product was soluble in EXCEL HC 100 at 10 weight % at 100° C., but precipitated at room temperature after 30 minutes.

Example 13

Adduct of Example 12 Product with Methyl Propiolate

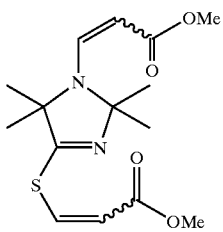

A mixture of the product made in Example 12 (0.1 g, 0.6 mmol) and methyl propiolate (0.053 g, 0.6 mmol) in deuterated chloroform (CDCl$_3$, 1 mL) was left at room temperature 3 days and then heated for 40h at 45° C. Solvent evaporation yielded RM-297 as a light-yellow, crystalline solid (1.5 g, 99%). IR: 2974, 1701, 1683, 1617, 1602, 1454 cm$^{-1}$; $^1$H NMR (CDCl$_3$, 500 MHz): δ8.29 (d, J=16.0 Hz), 8.08 (d, J=10 Hz), 8.075 (d, J=10 Hz), 7.36 (d, J=15 Hz), 6.09 (d, J=16 Hz), 6.08 (d, J=10 Hz), 6.03 (d, J=10 Hz), 4.73 (d, J=15 Hz), 3.71–3.69 (4 s, —CH$_3$), 1.48, 1.44, 1.34, 1.29 (4 s, —CH$_3$) ppm. The cis/trans ratio in the side chain attached to sulfur is 85/15, and in that attached to nitrogen it is 5/95. The product was soluble in EXCEL HC 100 at less than 5 weight % at 100° C.

Example 14

Adduct of DDPT with Methyl Propiolate

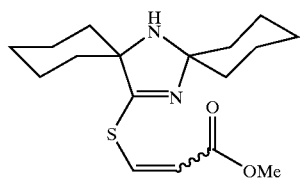

A mixture of DDPT (0.06 g, 0.252 mmol) and methyl propiolate (0.063 g, 0.75 mmol) in deuterated chloroform (CDCl$_3$, 1 mL)was heated at 45° C. for 24 h followed by standing at room temperature for 3 days. Solvent evaporation yielded the product depicted above as a light-yellow, crystalline solid (0.08 g, 99%). IR: 2932, 2854, 1716, 1603, 1448 cm$^{-1}$; $^1$H NMR (CDCl$_3$, 500 MHz): δ8.35 (d, J=15.1 Hz, 0.4 H), 8.25 (d, J=10 Hz, 0.6 H), 6.15 (d, J=15.1 Hz, 0.4 H), 6.07 (d, J=10 Hz, 0.6 H), 3.71 (s, —CH$_3$), 3.75 (s, —CH$_3$), 3.72 (s, —CH$_3$), 1.9–1.1 (m, 20 H) ppm; $^{13}$C NMR (CDCl$_8$, 125 MHz): δ170.9, 169.3, 166.9, 165.3, 153.0, 141.6, 141.0, 118.4, 115.1, 91.5, 91.0, 74.9, 74.3, 72.5, 72.5, 52.9, 51.6, 51.5, 36.7, 36.6, 25.4, 25.3, 25.0, 23.4, 23.3, 22.14, 22.12 ppm. The cis/trans ratio was 60/40. The product was soluble in EXCEL HC 100 at 5 weight % at 40° C.; ca. 10 weight % at 100° C. A small amount of solid precipitated after 30 minutes.

Example 15

Adduct of TMIT and an Imine Mixture

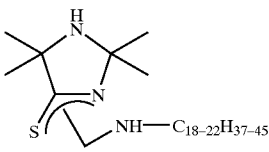

A mixture of TMIT (0.5 g, 3.16 mmol) and the formaldehyde imine (1.17 g, 3.2 mmol) of a mixture of branched C$_{18}$–C$_{22}$ primary amines (mixture of amines available from Rohm and Haas Co. under the name PRIMENE®JM-T) was heated in a sample vial at 120° C. for 1 h and the obtained liquid was cooled to room temperature yielding a thick syrup. IR: 3302, 1672, 1481, 1465, 1377 cm$^{-1}$; $^1$H NMR (CDCl$_3$, 500 MHz): δ5.4 (bm), 5.1 (s), 4.45–4.33 (5 s), 1.56–0.81 (3 m) ppm; $^{13}$C NMR (CDCl$_3$, 125 MHz): δ208.4, 208.0, 206.5, 82.78, 82.42, 78.05, 70.88, 69.58, 69.42, 69.27, 68.35, 54.95, and several peaks at 40–14 ppm. The product was soluble in EXCEL HC 100 at 10 weight % at 100° C.; at room temperature, 5% of the solid precipitated overnight.

What is claimed is:

1. A compound having the formula

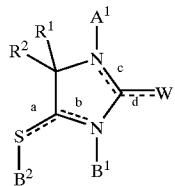

wherein W represents two groups, $R^3$ and $R^4$; bonds a and b are single or double bonds, provided that one of a and b is a single bond and the other is a double bond; c is a single bond, and d is two single bonds, $A^1$, $B^1$ and $B^2$ are independently hydrogen,

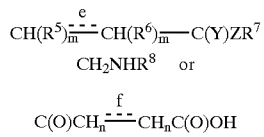

provided that $B^1$ is absent when b is a double bond, $B^2$ is absent when a is a double bond, $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; Y is O or S; Z is O, S or $NR^9$; m is 0 when bond e is a double bond and 1 when e is a single bond; n is 1 when bond f is a double bond and 2 when f is a single bond; $R^5$ is $C(Y)ZR^7$, hydrogen or $C_1$–$C_4$ alkyl; $R^6$ is hydrogen or $C_1$–$C_4$ alkyl; $R^7$, $R^8$ and $R^9$ are independently hydrogen, alkyl, alkenyl, aryl or aralkyl;

provided that at least one of $A^1$, $B^1$ and $B^2$ is present and is not hydrogen.

2. The compound of claim 1 in which $A^1$, $B^1$ and $B^2$ are independently hydrogen;

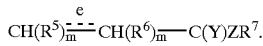

3. A composition comprising a lubricating oil and from 0.1% to 20% of a compound having the formula

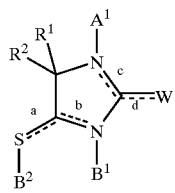

wherein W represents two groups, $R^3$ and $R^4$; bonds a and b are single or double bonds, provided that one of a and b is a single bond and the other is a double bond; c is a single bond, and d is two single bonds, $A^1$, $B^1$ and $B^2$ are independently hydrogen,

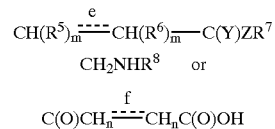

provided that $B^1$ is absent when b is a double bond, $B^2$ is absent when a is a double bond $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; Y is O or S; Z is O, S or $NR^9$; m is 0 when bond e is a double bond and 1 when e is a single bond; n is 1 when bond f is a double bond and 2 when f is a single bond; $R^5$ is $C(Y)ZR^7$, hydrogen or $C_1$–$C_4$ alkyl; $R^6$ is hydrogen or $C_1$–$C_4$ alkyl; $R^7$, $R^8$ and $R^9$ are independently hydrogen, alkyl, alkenyl, aryl or aralkyl;

provided that at least one of $A^1$, $B^1$ and $B^2$ is present and is not hydrogen.

4. The composition of claim 3 in which $A^1$, $B^1$ and $B^2$ are independently hydrogen; or

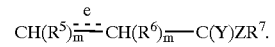

5. The composition of claim 4 which contains from 0.5% to 10% of said compound.

6. A method of improving anti-wear and anti-corrosion characteristics of a lubricating oil by adding from 0.1% to 20% of a compound having the formula

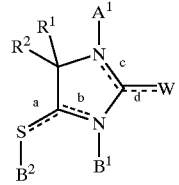

wherein W represents two groups, $R^3$ and $R^4$; bonds a and b are single or double bonds, provided that one of a and b is a single bond and the other is a double bond; c is a single bond, and d is two single bonds, $A^1$, $B^1$ and $B^2$ are independently hydrogen,

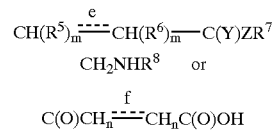

provided that $B^1$ is absent when b is a double bond, $B^2$ is absent when a is a double bond $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; Y is O or S; Z is O, S or $NR^9$; m is 0 when bond e is a double bond and 1 when e is a single bond; n is 1 when bond f is a double bond and 2 when f is a single bond; $R^5$ is $C(Y)ZR^7$, hydrogen or $C_1$–$C_4$ alkyl; $R^6$ is hydrogen or $C_1$–$C_4$ alkyl; $R^7$, $R^8$ and $R^9$ are independently hydrogen, alkyl, alkenyl, aryl or aralkyl;

provided that at least one of $A^1$, $B^1$ and $B^2$ is present and is not hydrogen.

7. The method of claim 6 in which $A^1$, $B^1$ and $B^2$ are independently hydrogen; or

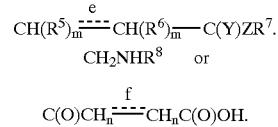

8. The compound of claim 2 in which $A^1$, $B^1$ and $B^2$ are independently hydrogen or $CHR^5CHR^6C(O)OR^7$, wherein $R^5$ and $R^6$ are hydrogen or $C_1$–$C_4$ alkyl.

9. The compound of claim 8 in which $A^1$ is hydrogen, and $B^1$ and $B^2$ are independently hydrogen or $CH_2CH_2C(O)O$-alkyl.

10. The compound of claim 4 in which $A^1$, $B^1$ and $B^2$ are independently hydrogen or $CHR^5CHR^6C(O)OR^7$, wherein $R^5$ and $R^6$ are hydrogen or $C_1$–$C_4$ alkyl.

11. The compound of claim 10 in which $A^1$ is hydrogen, and $B^1$ and $B^2$ are hydrogen or $CH_2CH_2C(O)O$-alkyl.

12. The compound of claim 7 in which $A^1$, $B^1$ and $B^2$ are independently hydrogen or $CHR^5CHR^6C(O)OR^7$, wherein $R^5$ and $R^6$ are hydrogen or $C_1$–$C_4$ alkyl.

13. The compound of claim 12 in which $A_1$ is hydrogen, and $B^1$ and $B^2$ are independently hydrogen or $CH_2CH_2C(O)O$-alkyl.

* * * * *